United States Patent
Yoshida et al.

(10) Patent No.: US 10,781,464 B2
(45) Date of Patent: Sep. 22, 2020

(54) METHOD FOR PRODUCING FATTY ACID ESTER

(71) Applicants: KANSAI CHEMICAL ENGINEERING CO., LTD., Amagasaki-shi, Hyogo (JP); BIO-ENERGY CORPORATION, Amagasaki-shi, Hyogo (JP)

(72) Inventors: Ayumi Yoshida, Amagasaki (JP); Shinji Hama, Amagasaki (JP); Hideo Noda, Amagasaki (JP)

(73) Assignee: Kansai Chemical Engineering Co., Ltd., Hyogo (JP)

( * ) Notice: Subject to any disclaimer, the term of this patent is extended or adjusted under 35 U.S.C. 154(b) by 0 days.

(21) Appl. No.: 15/552,111

(22) PCT Filed: Jul. 1, 2016

(86) PCT No.: PCT/JP2016/069694
§ 371 (c)(1),
(2) Date: Jan. 23, 2018

(87) PCT Pub. No.: WO2017/006876
PCT Pub. Date: Jan. 12, 2017

(65) Prior Publication Data
US 2018/0216143 A1 Aug. 2, 2018

(30) Foreign Application Priority Data
Jul. 3, 2015 (JP) ................. 2015-134782

(51) Int. Cl.
*C12P 7/64* (2006.01)
*C12P 7/62* (2006.01)
*C11C 3/00* (2006.01)
*C12N 9/20* (2006.01)

(52) U.S. Cl.
CPC ............ *C12P 7/6436* (2013.01); *C11C 3/003* (2013.01); *C12P 7/62* (2013.01); *C12N 9/20* (2013.01); *C12Y 301/01003* (2013.01); *Y02E 50/13* (2013.01)

(58) Field of Classification Search
CPC .......... C12P 7/6436; C12P 7/62; C11C 3/003; Y02E 50/13; C12N 9/20
See application file for complete search history.

(56) References Cited

U.S. PATENT DOCUMENTS

| 2008/0045606 A1 | 2/2008 | Schoerken et al. |
| 2008/0153143 A1 | 6/2008 | Schorken et al. |
| 2014/0120589 A1 | 5/2014 | Austic et al. |

FOREIGN PATENT DOCUMENTS

| JP | 2008526265 A | 7/2008 |
| JP | 2008527154 A | 7/2008 |

OTHER PUBLICATIONS

Meher et al. Technical aspects of biodiesel production by transesterification—a review. Renewable and Sustainable Energy Reviews (2006), v10(3), p. 248-268. (Year: 2006).*
H. Strathmann. Chapter 2 in Ion-Exchange Membrane Separation Processes, vol. 9 (Membrane Science and Technology (2004), ISBN: 0-111-50236-X (Year: 2004).*
Li et al. Pretreatment of immobilized *Candida* sp. 99-125 lipase to improve its methanol tolerance for biodiesel production. Journal of Molecular Catalysis B: Enzymatic (2010), 62, 15-18. (Year: 2010).*
Nordblad et al., "Identification of Critical Parameters in Liquid Enzyme-Catalyzed Biodiesel Production", Biotechnology and Bioengineering, vol. 111, No. 12, pp. 2446-2453, Dec. 2014.
Cesarini et al., "Exploring a new, soluble lipase for FAMEs production in water-containing systems using crude soybean oil as a feedstock", Process Biochemistry, vol. 48, pp. 484-487 (2013).
Cesarini et al., "Combining phospholipases and a liquid lipase for one-step biodiesel production and crude oils", Biotechnology for Biofuels, 7:29, pp. 1-12 (2014).
Chen et al., "Effect of several factors on soluble lipase-mediated biodiesel preparation in the biphasic aqueous-oil systems", World J. Microbiol Biotechnol, vol. 24, pp. 2097-2102 (2008).
Li et al., "Effect of phospholipids on free lipase-mediated methanolysis for biodiesel production", Journal of Molecular Catalysis B: Enzymatic, vol. 91, pp. 67-71 (2013).
Li et al., "Free lipase-catalyzed biodiesel production from phospholipids-containing oils", Biomass and Bioenergy, vol. 71, pp. 162-169 (2014).
Li et al., "Exploration on the effect of phospholipids on free lipase-mediated biodiesel production", Journal of Molecular Catalysis B: Enzymatic, vol. 102, pp. 88-93 (2014).
Du et al., "Mechanism study on NS81006-mediated methanolysis of triglyceride in oil/water biphasic system for biodiesel production", Process Biochemistry, vol. 45, pp. 446-450 (2010).
Pedersen et al., "Batch production of FAEE-biodiesel using a liquid lipase formulation", Journal of Molecular Catalysis B: Enzymatic, vol. 105, pp. 89-94 (2014).
Price et al., "Mechanistic Modeling of Biodiesel Production Using a Liquid Lipase Formulation", Biotechnol. Prog., vol. 30, No. 6, pp. 1277-1290 (2014).

(Continued)

*Primary Examiner* — Sean C. Barron
(74) *Attorney, Agent, or Firm* — Ajay A. Jagtiani; Miles & Stockbridge P.C.

(57) ABSTRACT

A method for producing a fatty acid ester according to the present invention includes mixing a raw fat or oil, a liquid enzyme, and an alcohol having 1 to 8 carbon atoms in the presence of water and an electrolyte. According to the present invention, a fatty acid ester can be efficiently produced via a transesterification reaction without using any expensive buffer solution or amphipathic substance. Furthermore, in the reaction, it is not necessarily required to agitate reactants at a high speed, which makes the present invention adaptive to various production facilities and conditions.

7 Claims, 5 Drawing Sheets

(56) References Cited

OTHER PUBLICATIONS

Ren et al., "Study on Free Lipase-Catalyzed Ethanolysis for Biodiesel Preparation in an Oil/Water Biphasic System", J. Am. Oil Chem. Soc., vol. 88, pp. 1551-1555 (2011).

Ren et al., "Free Lipase-Catalyzed Esterification of Oleic Acid for Fatty Acid Ethyl Ester Preparation with Response Surface Optimization", J. Am. Oil Chem. Soc., vol. 90, pp. 73-79 (2013).

Amoah et al., "Lipase cocktail for efficient conversion of oils containing phospholipids to biodiesel", Bioresource Technology, vol. 211, pp. 224-230 (2016).

Bueso et al., "Lipase-catalyzed biodiesel production and quality with Jatropha curcas oil: exploring its potential for Central America", Journal of Biological Engineering, 9:12, pp. 1-7 (2015).

Firdaus et al., "Development of kinetic model for biodiesel production using liquid lipase as a biocatalyst, esterification step", Biochemical Engineering Journal, vol. 105, pp. 52-61 (2016).

Li et al., "Kinetic study on free lipase NS81006-catalyzed biodiesel production from soybean oil", Journal of Molecular Catalysis B: Enzymatic, vol. 121, pp. 22-27 (2015).

Li et al., "Efficient biodiesel production from phospholipids-containing oil: Synchronous catalysis with phospholipase and lipase", Biochemical Engineering Journal, vol. 94, pp. 45-49 (2015).

Nielsen et al., "Production of Biodiesel Using Liquid Lipase Foundations", J. Am. Oil Chem. Soc., vol. 93, pp. 905-910 (2016).

International Search Report received in PCT/JP2016/069694 dated Sep. 20, 2016.

M. Norblad et al., "Identification of Critical Parameters in Liquid Enzyme-Catalyzed Biodiesel Production," Biotechnology and Bioengineering, 2014, vol. 11, No. 12, pp. 2446-2453 (abstract).

R.R. Nasaruddin et al., "Enzymatic Biodiesel Production from Sludge Palm Oil (SPO) Using Locally Produced Candida Cylindracea Lipase," African J. of Biotechnology, 2013, vol. 12 (31), pp. 4966-4974.

K. Nie et al., "Additives Improve the Enzymatic Synthesis of Biodiesel from Waste Oil in a Solvent Free System," Fuel, 2015, vol. 146, pp. 13-19 (abstract).

Seibutsu-kogaku Kaishi, "Scale-up of an Enzymatic Biodiesel Production System," 2014, vol. 92, No. 6, pp. 262-269 (abstract).

* cited by examiner

[Figure 1]
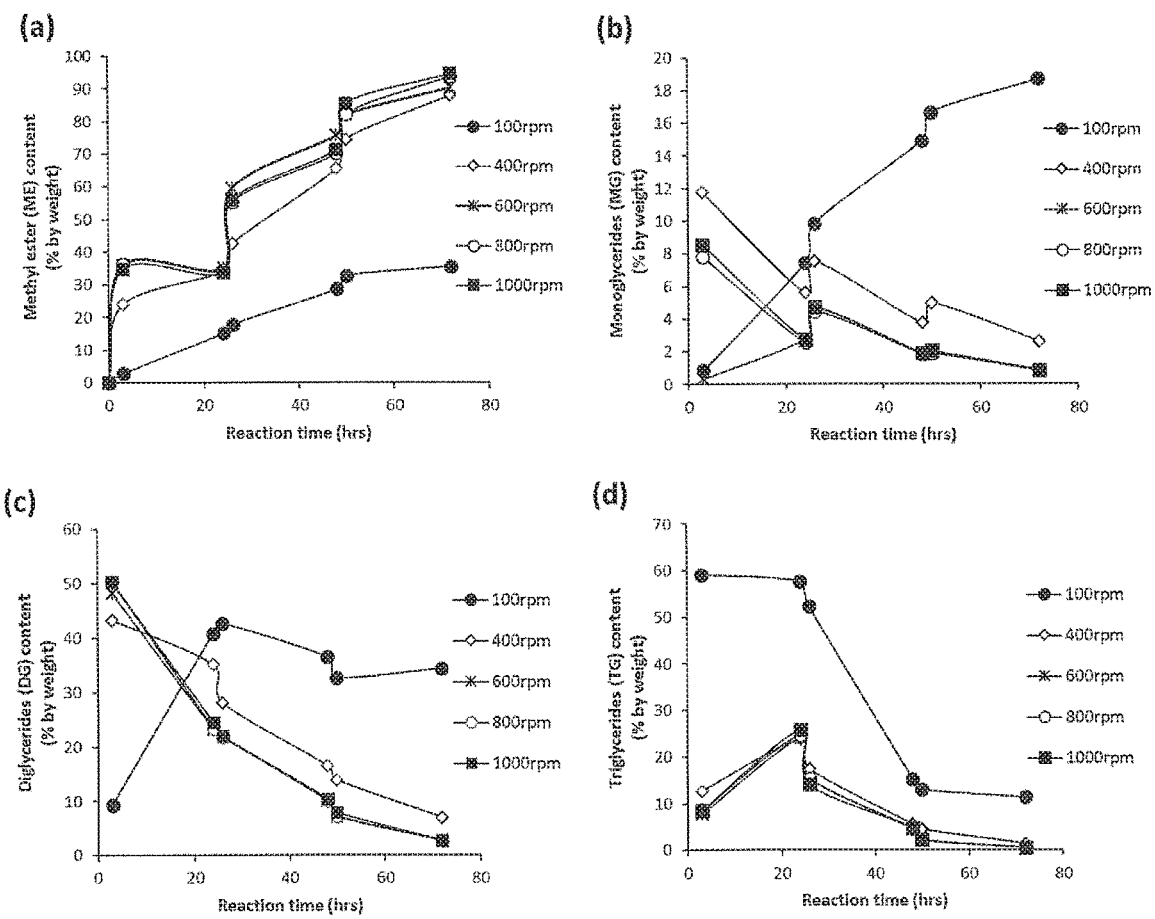
[Figure 2]
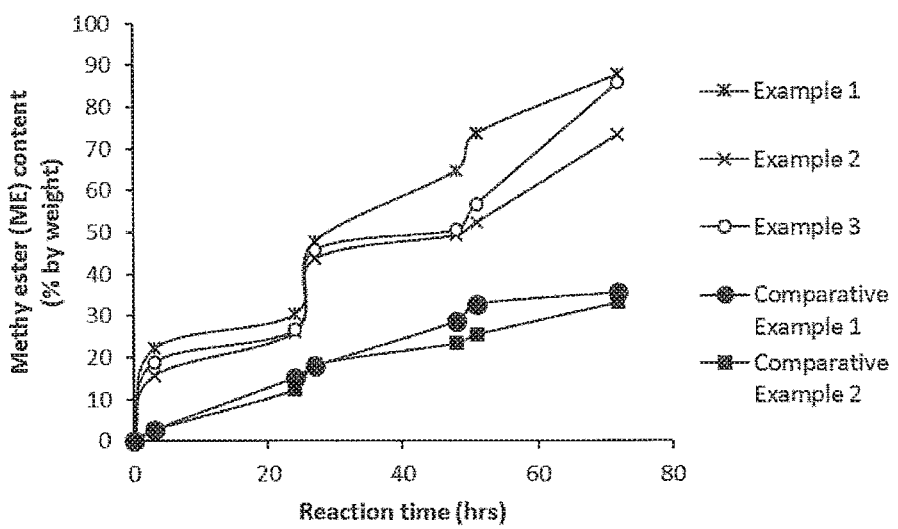

[Figure 3]
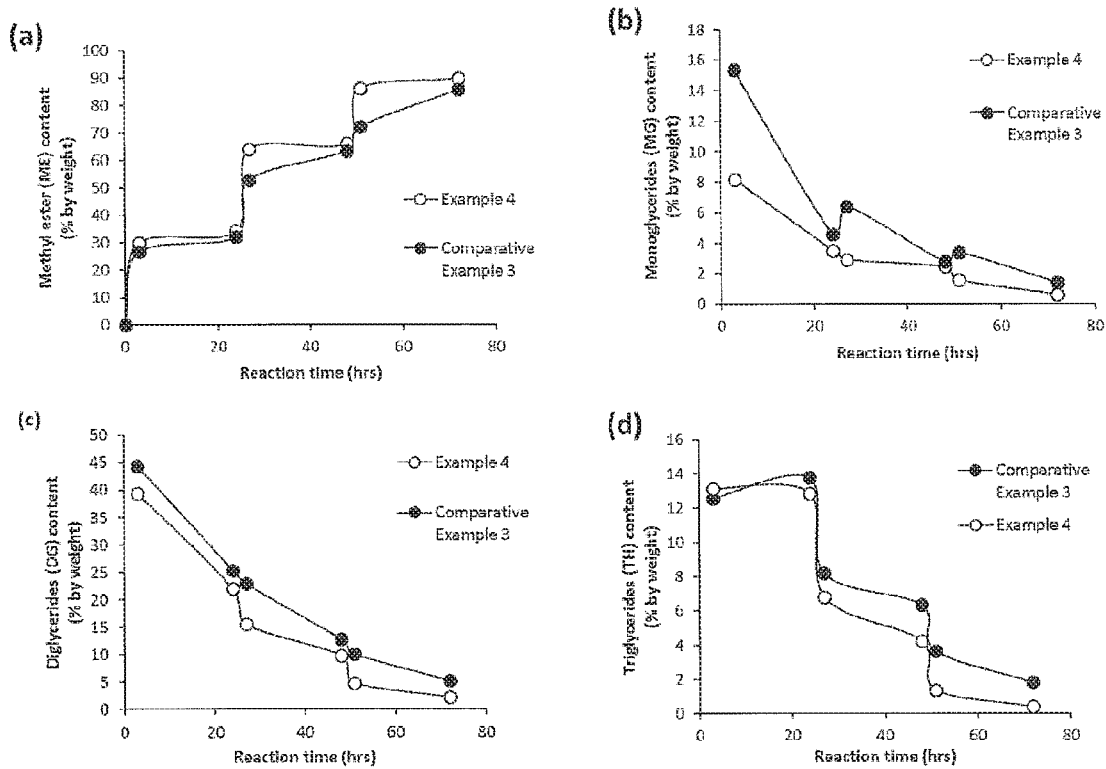
[Figure 4]
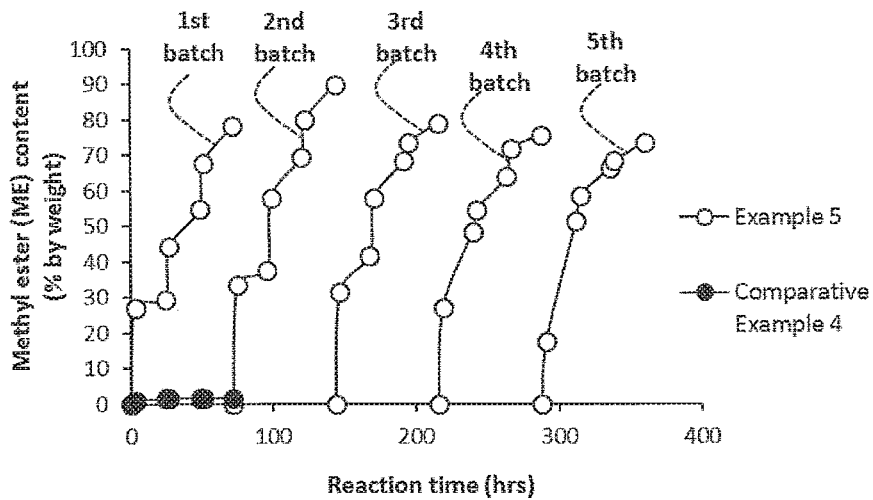

[Figure 5]
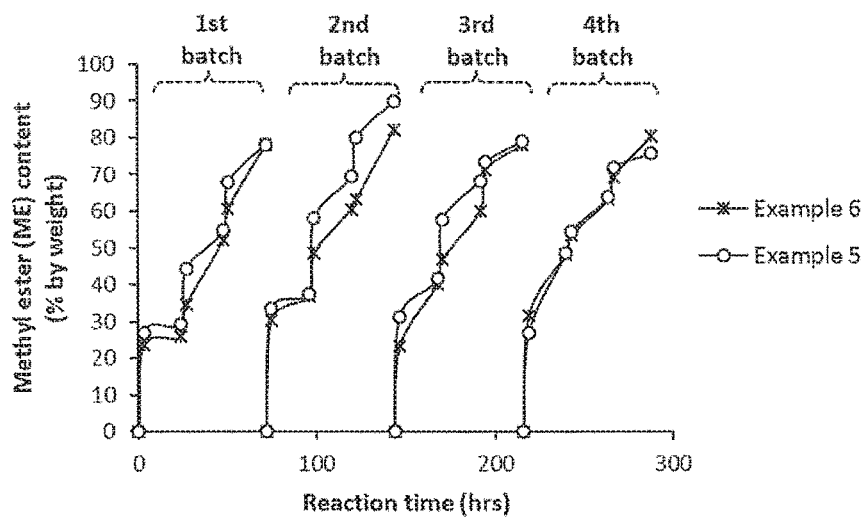
[Figure 6]
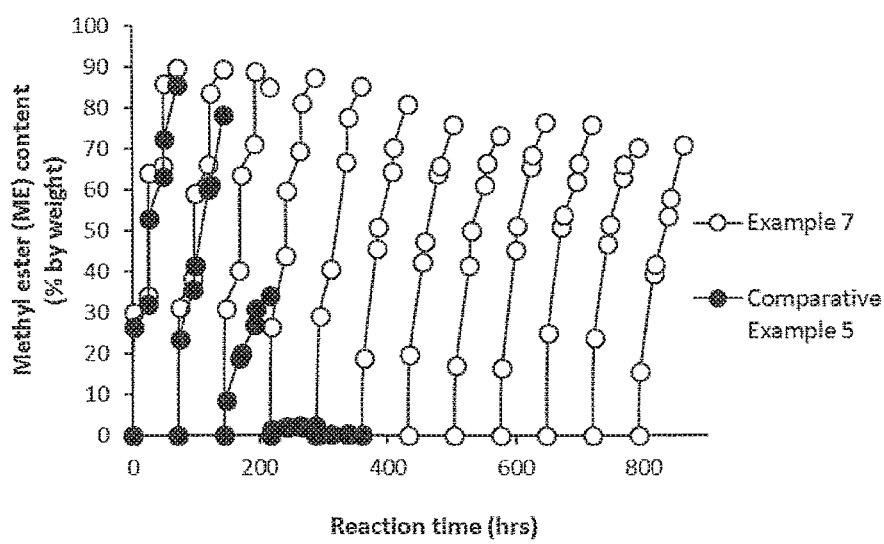

[Figure 7]
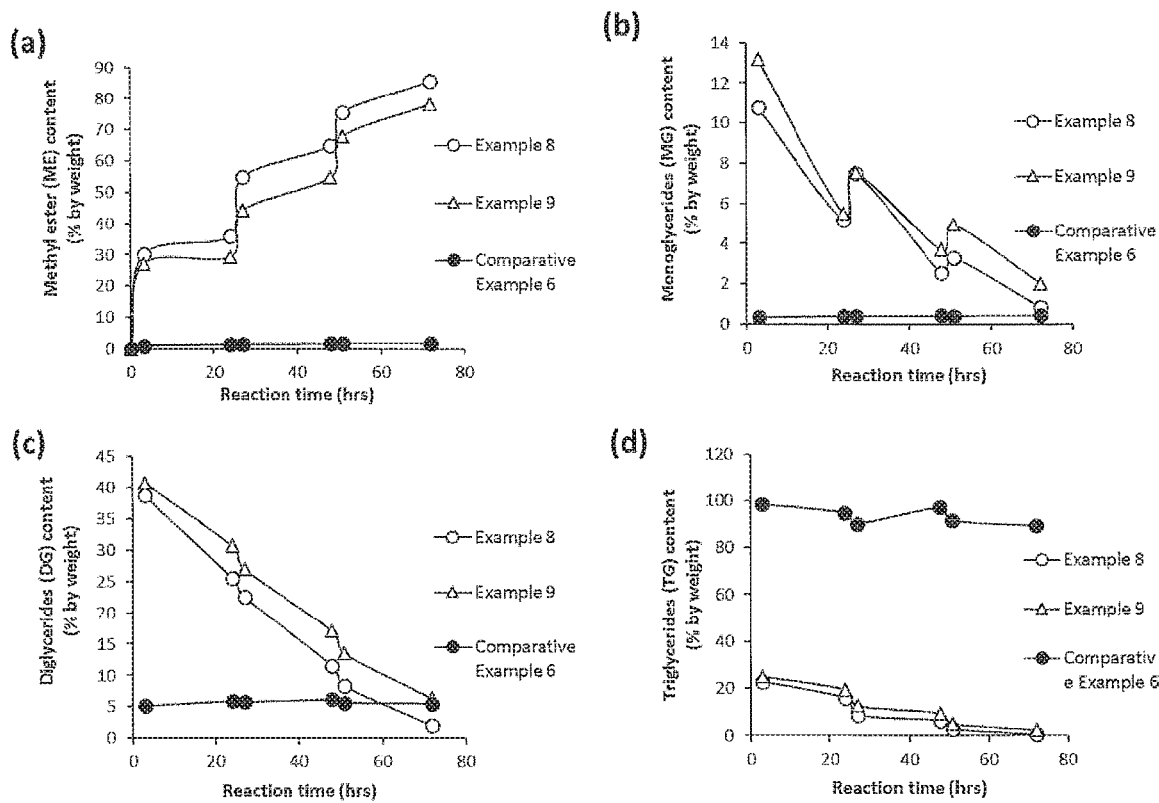
[Figure 8]
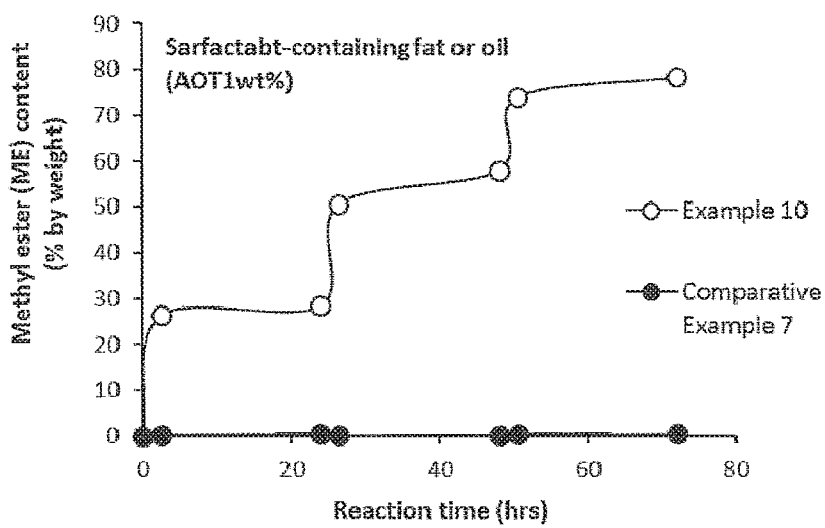

[Figure 9]
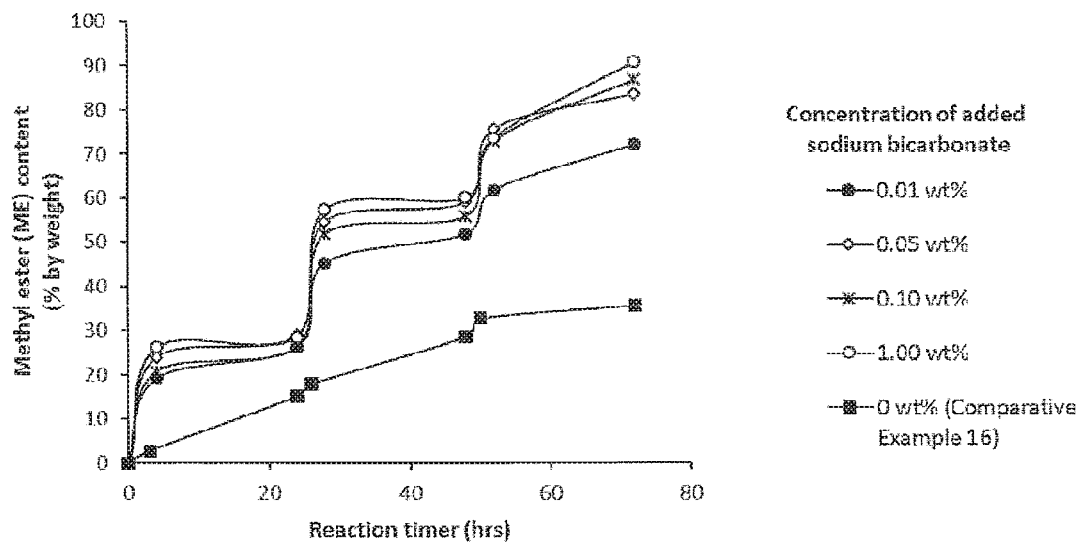
[Figure 10]
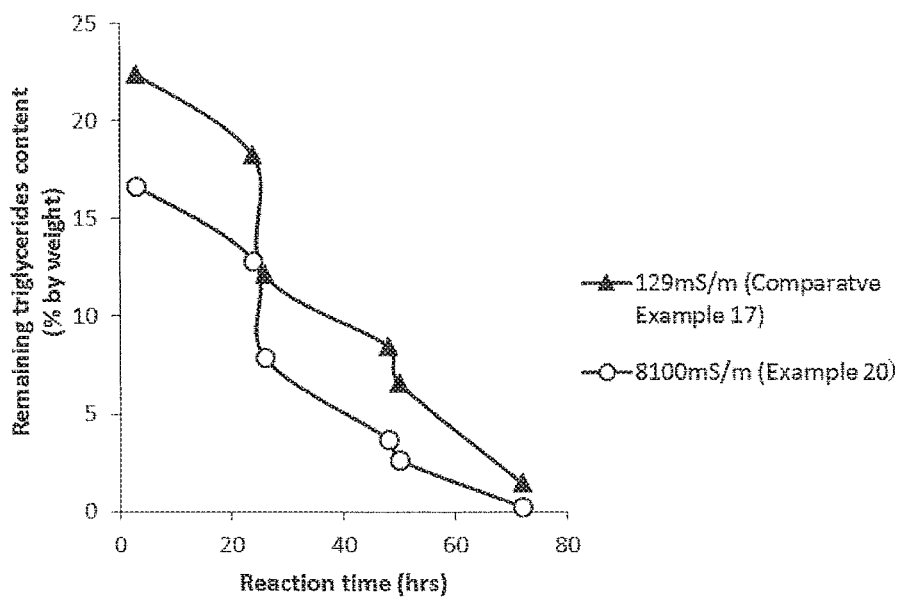

METHOD FOR PRODUCING FATTY ACID ESTER

TECHNICAL FIELD

The present invention relates to a method for producing a fatty acid ester, and more specifically relates to a method for producing a fatty acid ester by using a liquid enzyme.

BACKGROUND ART

Oils and fats have a basic structure in which glycerin and a fatty acid bind together, and are used for various industrial uses. Furthermore, fats and oils are also a type of foods that are necessary for life.

Recently, fats and oils have also been attracting attention as raw materials to be converted to fuels or chemicals. In particular, attempts to synthesize a long-chain fatty acid ester from an animal fat or oil and/or a vegetable fat or oil via a chemical reaction and use the synthesized long-chain fatty acid ester as a biodiesel fuel that can substitute for gas oil have been actively made.

For biodiesel fuel production, for example, it has been proposed to use a transesterification reaction based on an enzyme-catalyzed process in which a liquid enzyme such as lipase is employed as a catalyst. A liquid enzyme is constituted by a concentrated and refined culture solution. In this respect, liquid enzymes are inexpensive compared with immobilized enzymes. Moreover, such an enzyme remains in glycerin, which is a by-product of the transesterification reaction, and can therefore be used for the reaction of the next batch. Thus, the liquid enzyme can be repeatedly used, and the costs of biodiesel fuel production can be reduced (Non-Patent Document 1).

A transesterification reaction using a liquid enzyme is performed in a two-phase system consisting of an oil layer and a water layer. Therefore, for example, it is required to add water to the reaction system in an amount of about 5% by weight relative to the weight of the reaction system.

However, in the transesterification reaction, in order to increase the reaction efficiency, it is required to form an emulsion by agitating reactants at a high speed. Moreover, it also has been reported that unreacted glycerides such as monoglycerides (MG), diglycerides (DG), and triglycerides (TG) are likely to remain in the resulting product (Non-Patent Document 1).

On the other hand, heretofore, it has been reported that, in a transesterification reaction, the addition of a buffer solution (e.g., phosphate buffer solution with adjusted pH) to a fat or oil enhances the enzyme catalyst activity and hence improves the reaction efficiency (Non-Patent Document 2). However, there is concern that, with this method, the buffer solution that is used increases the cost of biodiesel fuel production.

Moreover, it also has been reported that the addition of an amphipathic substance such as a surfactant to the reaction system of a transesterification reaction promotes emulsion formation and hence improves the reaction efficiency (Non-Patent Document 3). However, there is concern that, with this method, the amphipathic substance is expensive and also causes difficulties in separation from the by-product glycerin after the completion of the reaction.

RELATED ART DOCUMENTS

Non-Patent Documents

[Non-Patent Document 1] M. Nordblad et al., Biotechnology and Bioengineering, 2014, Vol. 11, No. 12, pp. 2446-2453

[Non-Patent Document 2] R. R. Nasaruddin et al., Afr. J. Biotechnol., 2013, Vol. 12 (31), pp. 4966-4974

[Non-Patent Document 3] K. Nie et al., Fuel, 2015, Vol. 146, pp. 13-19

SUMMARY OF THE INVENTION

Problem to be Solved by the Invention

The present invention was made to address the above-described problems, and it is an object thereof to provide a method for producing a fatty acid ester with which the formation of an emulsion of an oil layer and a water layer in a transesterification reaction can be promoted, and the reaction efficiency can be improved.

Means for Solving the Problem

The present invention provides a method for producing a fatty acid ester comprising:

mixing a raw fat or oil, a liquid enzyme, and an alcohol having 1 to 8 carbon atoms in the presence of water and an electrolyte.

In one embodiment, the water and the electrolyte are added in the form of an aqueous electrolyte solution that has been prepared in advance.

In a further embodiment, the aqueous electrolyte solution has a conductivity of 30 mS/m to 5000 mS/m.

In one embodiment, the liquid enzyme is added together with the water and the electrolyte in the form of an enzyme solution that has been prepared in advance.

In one embodiment, the enzyme solution has a conductivity of 10 mS to 20000 mS/m.

In one embodiment, the electrolyte is at least one salt selected from the group consisting of sodium hydrogen carbonate, sodium carbonate, calcium chloride, calcium hydroxide, trisodium citrate, sodium hydrogen phosphate, sodium dihydrogen phosphate, sodium chloride, and trisodium phosphate.

In one embodiment, the raw fat or oil is at least one fat or oil selected from the group consisting of vegetable fats and oils, animal fats and oils, fish oils, fats and oils produced by microorganisms, and waste oils thereof.

In one embodiment, the raw fat or oil is a modified fat or oil that is obtained by mixing at least one fat or oil selected from the group consisting of vegetable fats and oils, animal fats and oils, fish oils, fats and oils produced by microorganisms, and waste oils thereof with glycerin derived from an enzyme-catalyzed process.

Effects of the Invention

According to the present invention, a fatty acid ester can be efficiently produced via a transesterification reaction without using any expensive buffer solution or amphipathic substance. Furthermore, in the reaction, it is not necessarily required to agitate reactants at a high speed, which makes the present invention adaptive to various production facilities and conditions.

BRIEF DESCRIPTION OF DRAWINGS

FIG. 1 shows graphs showing changes in the content of various components of reaction systems in transesterification reactions that were performed in Reference Example 1 under different conditions in terms of agitation speed: FIG. 1(a) is a graph showing changes in the content of methyl esters (ME) that were generated, FIG. 1(b) is a graph showing changes in the content of monoglycerides (MG) that were present in the reaction systems, FIG. 1(c) is a graph showing changes in the content of diglycerides (DG) that were present in the reaction systems, and FIG. 1(d) is a graph showing changes in the content of triglycerides (TG) that were present in the reaction systems.

FIG. 2 is a graph showing changes in the content of methyl esters (ME) generated in transesterification reactions that were performed in Examples 1 to 3 and Comparative Examples 1 and 2.

FIG. 3 shows graphs showing changes in the content of various components of reaction systems in transesterification reactions that were performed in Example 4 and Comparative Example 3: FIG. 3(a) is a graph showing changes in the content of methyl esters (ME) that were generated, FIG. 3(b) is a graph showing changes in the content of monoglycerides (MG) that were present in the reaction systems, FIG. 3(c) is a graph showing changes in the content of diglycerides (DG) that were present in the reaction systems, and FIG. 3(d) is a graph showing changes in the content of triglycerides (TG) that were present in the reaction systems.

FIG. 4 is a graph showing changes in the content of methyl esters (ME) generated in transesterification reactions that were performed in Example 5 and Comparative Example 4.

FIG. 5 is a graph showing changes in the content of methyl esters (ME) generated in transesterification reactions of first to fourth batches that were performed in Example 6, superimposed on the changes in the ME content obtained via the transesterification reactions of first to fourth batches obtained in Example 5.

FIG. 6 is a graph showing changes in the content of methyl esters (ME) generated in transesterification reactions that were performed in Example 7 and Comparative Example 5.

FIG. 7 shows graphs showing changes in the content of various components of reaction systems in transesterification reactions that were performed in Examples 8 and 9 and Comparative Example 6: FIG. 7(a) is a graph showing changes in the content of methyl esters (ME) that were generated, FIG. 7(b) is a graph showing changes in the content of monoglycerides (MG) that were present in the reaction systems, FIG. 7(c) is a graph showing changes in the content of diglycerides (DG) that were present in the reaction systems, and FIG. 7(d) is a graph showing the content of triglycerides (TG) that were present in the reaction systems.

FIG. 8 is a graph showing changes in the content of methyl esters (ME) generated in transesterification reactions that were performed in Example 10 and Comparative Example 7, and shows the changes in the ME content obtained in the transesterification reactions when a fat or oil containing a surfactant inhibiting the transesterification reactions was used.

FIG. 9 is a graph showing changes in the content of methyl esters (ME) generated in transesterification reactions that were performed in Example 19 and Comparative Example 16.

FIG. 10 is a graph showing changes in the content of methyl esters (ME) generated in transesterification reactions that were performed in Example 20 and Comparative Example 17.

MODES FOR CARRYING OUT THE INVENTION

The present invention will be described in detail below.

According to a method for producing a fatty acid ester of the present invention, first, a raw fat or oil, a liquid enzyme, and an alcohol having 1 to 8 carbon atoms are mixed in the presence of water and an electrolyte.

The raw fat or oil that is used in the present invention is, for example, a fat or oil that can be used to produce a fatty acid ester for biodiesel fuel. The raw fat or oil may be a preliminarily refined fat or oil or may be an unrefined fat or oil containing impurities.

Examples of the raw fat or oil include cooking fats and oils and waste cooking fats and oils thereof, crude oils, and other waste matter-based fats and oils, as well as combinations thereof.

Examples of the cooking fats and oils and waste cooking fats and oils thereof include vegetable fats and oils, animal fats and oils, fish oils, fats and oils produced by microorganisms, and waste oils thereof as well as mixtures (mixed fats and oils) thereof. Examples of the vegetable fats and oils include, but not necessarily limited to, soybean oil, rapeseed oil, palm oil, and olive oil. Examples of the animal fats and oils include, but not necessarily limited to, beef tallow, lard, chicken fat, whale oil, and mutton tallow. Examples of the fish oils include, but not necessarily limited to, sardine oil, tuna oil, and squid oil. Examples of the fats and oils produced by microorganisms include, but not necessarily limited to, fats and oils produced by microorganisms belonging to the genus *Mortierella,* the genus *Schizochytrium,* or the like.

Here, the term "waste oil" as used herein refers to a fat or oil that has been used in a food production process in the food industry or in a household or restaurant cooking process. Examples of the waste oils include oils that have been used in the production or cooking of processed foods such as tempura, fried chicken, and French fries. According to one embodiment, there are many cases where a waste oil has already been exposed to a high temperature through a certain use. Thus, in many cases, a waste oil contains a hydrogenated, oxidized, or peroxidized fat or oil component and impurities (e.g., water, salt, polar compounds, various polymers, and other solid foreign substances and the like). The impurities may function as inhibitory substances of the above-described transesterification reaction. However, waste oils can also be used as the raw fat or oil of the present invention.

Examples of the crude oils that can be used in the present invention include unrefined or unprocessed fats and oils that are obtained from a conventional oil expression step for cooking fats and oils, and the crude oils may contain, for example, gum-like impurities, such as phospholipids and/or proteins, free fatty acids, pigments, trace metals, and other hydrocarbon impurities that are soluble in oil, as well as combinations thereof. The amount of impurities contained in a crude oil is not limited.

Examples of the other waste matter-based fats and oils that can be used in the present invention include oil foots obtained as a result of refining, in the presence of an alkali, raw oil that is produced during the production of a food fat or oil, heat-treatment oil, press oil, and rolling oil, as well as combinations thereof.

The raw fat or oil that can be used in the present invention may have any acid value. The "acid value" is one of chemical analysis values for fats and oils, and the acid value of a fat or oil is expressed as the number of milligrams of potassium hydroxide required to neutralize the free fatty acids present in 1 g of the fat or oil. Therefore, it is considered that higher acid values of fats and oils generally indicate higher degrees of deterioration, and lower acid values of fats and oils indicate higher degrees of quality. For example, during biodiesel fuel production, the acid value of a fat or oil that can be employed in a single transesterification reaction using an alkaline catalyst is not more than 2.0 mg-KOH/g fat or oil, and the types of raw fats and oils that satisfy such an acid value are extremely limited. In contrast, with regard to the raw fat or oil that can be used in the present invention, for example, a raw fat or oil having an acid value exceeding 2.0 mg-KOH/g fat or oil can also be used. In the present invention, fats and oils having a wider range of acid values, for example, fats and oils having an acid value of not more than 50 mg-KOH/g fat or oil, and preferably not more than 10 mg-KOH/g fat or oil can be used, because such fats and oils are easily available and can reduce the production costs, for example.

The raw fat or oil of the present invention may contain water in any amount, as long as the water does not inhibit the inherent characteristics of the fat or oil. Furthermore, an unreacted fat or oil remaining in a solution that has been used in a separate reaction for forming a fatty acid ester may also be used as the raw fat or oil.

According to one embodiment of the present invention, a fat or oil (hereinafter also referred to as the modified fat or oil) obtained by mixing a fat or oil such as those described above with glycerin derived from an enzyme-catalyzed process may also be used as the raw fat or oil.

The glycerin derived from an enzyme-catalyzed process is a by-product that has been obtained along with a fatty acid ester through a fatty acid ester generating reaction (an ester reaction that has been separately performed in advance to generate a fatty acid ester; hereinafter sometimes referred to as "the previous reaction") using the above-described fat or oil as well as a liquid enzyme and an alcohol, which will be described later, and preferably, the glycerin derived from an enzyme-catalyzed process is a crude product of the fatty acid ester generating reaction. There is no limitation on the type and amount of the raw fat or oil, the liquid enzyme, and the alcohol used in the previous reaction that has been performed to obtain the glycerin derived from an enzyme-catalyzed process.

The amount of glycerin derived from an enzyme-catalyzed process that can be used to obtain a modified fat or oil varies in accordance with, for example, the type and/or amount of the above-described fat or oil and is therefore not necessarily limited, but may be preferably 1 part by weight to 100 parts by weight, and preferably 4 parts by weight to 50 parts by weight, relative to 100 parts by weight of the fat or oil. When the amount of glycerin that is used is less than 1 part by weight, there is a risk that a sufficient reduction in the acid value of the resulting fat or oil may be difficult. When the amount of glycerin that is used exceeds 100 parts by weight, the acid value of the resulting fat or oil may be unchanged, but rather there is a risk that the production efficiency may be reduced.

The fat or oil and the glycerin derived from an enzyme-catalyzed process are mixed in the following manner: for example, the fat or oil and the glycerin are added into a single reaction container simultaneously or in any order, and mixed preferably under agitation. The temperature that is applied during the mixing is not necessarily limited, but may be, for example, 5° C. to 100° C., preferably 10° C. to 80° C., and more preferably 25° C. to 80° C. The time required for the mixing varies in accordance with the type and amount of the fat or oil and the glycerin derived from an enzyme-catalyzed process that are used, the type and amount of impurities contained in the raw fat or oil, and the like and is therefore not necessarily limited. A person skilled in the art can select any desired period of time.

The thus obtained modified fat or oil can also be used as the raw fat or oil in the present invention. The acid value of the modified fat or oil is suppressed to a low level irrespective of the acid value of the raw fat or oil that has been used to produce the modified fat or oil. Therefore, in the method for producing a fatty acid ester of the present invention, the possibility of saponification occurring in the reaction system and/or the possibility of a reduction in the reaction efficiency can be reduced.

With regard to the liquid enzyme that is used in the present invention, enzyme catalysts that have the properties of liquid at room temperature, of any enzyme catalysts that can be used for a fatty acid ester generating reaction can be used. Examples of the liquid enzyme include lipase, cutinase, and combinations thereof.

Here, the term "lipase" as used herein refers to an enzyme that has the ability to act on a glyceride (also called acylglycerol) and degrade the glyceride into glycerin or a partial glyceride and a fatty acid, and also has the ability to generate a fatty acid ester via transesterification in the presence of a linear lower alcohol.

The lipase that can be used in the present invention may be 1,3-specific or may be nonspecific. In terms of the capability of producing a linear lower alcohol ester of a fatty acid, it is preferable that the lipase is nonspecific. Examples of the lipase that can be used in the present invention include lipases derived from filamentous fungi belonging to the genus *Rhizomucor* (*Rhizomucor miehei*), the genus *Mucor*, the genus *Aspergillus*, the genus *Rhizopus*, the genus *Penicillium*, and the like; lipases derived from yeasts belonging to genus *Candida* (*Candida antarctica*, *Candida rugosa*, and *Candida cylindracea*), *Pichia*, and the like; lipases derived from bacteria belonging to the genus *Pseudomonas*, the genus *Serratia*, and the like; and lipases derived from animals, such as hog pancreas. Liquid lipase can be obtained by, for example, concentrating and refining a culture solution of any of the above-described microorganisms containing lipase produced by that microorganism or by dissolving powdered lipase in water. A commercially available liquid lipase can also be used. An example of the commercially available liquid lipase is a lipase (Callera Trans L; manufactured by Novozymes) derived from *Thermomyces lanuginosus*.

The amount of the above-described liquid enzyme used in the present invention varies in accordance with, for example, the type and/or amount of raw fat or oil and is therefore not necessarily limited, but may be preferably 0.1 parts by weight to 50 parts by weight, and preferably 0.2 parts by weight to 30 parts by weight, relative to 100 parts by weight of raw fat or oil that is used. When the amount of liquid enzyme that is used is less than 0.1 parts by weight, an effective transesterification reaction cannot be catalyzed, and there is thus a risk that the yield and/or the percentage yield of a desired fatty acid ester may be reduced. When the amount of liquid enzyme that is used exceeds 50 parts by weight, the yield and/or the percentage yield of the desired fatty acid ester that is obtained through the transesterification reaction no longer changes, but rather there is a risk that the production efficiency may be reduced.

In the present invention, the above-described liquid enzyme can be repeatedly used in transesterification reactions. That is to say, after the liquid enzyme has been subjected once to a transesterification reaction according to the method of the present invention, and a desired product (fatty acid ester) has been removed from the reaction system, the liquid enzyme remains in the residue together with glycerin, which is a by-product. The remaining liquid enzyme can be, for example, extracted together with the glycerin and used in the next new transesterification reaction. In this manner, the liquid enzyme can be repeatedly used in, for example, two to twenty, and preferably two to ten transesterification reactions.

The alcohol that is used in the present invention is a linear or branched lower alcohol (e.g., an alcohol having 1 to 8 carbon atoms, and preferably an alcohol having 1 to 4 carbon atoms). A linear lower alcohol is preferable. Examples of the linear lower alcohol that can be used in the present invention include, but not necessarily limited to, methanol, ethanol, n-propanol, and n-butanol, as well as combinations thereof.

The amount of the above-described alcohol that is used in the present invention varies in accordance with, for example, the type and/or amount of raw fat or oil that is used and is therefore not necessarily limited, but may be preferably 5 parts by weight to 100 parts by weight, and preferably 10 parts by weight to 30 parts by weight, relative to 100 parts by weight of raw fat or oil. When the amount of alcohol that is used is less than 5 parts by weight, an effective transesterification reaction cannot be realized, and there is thus a risk that the yield and/or the percentage yield of a desired fatty acid ester may be reduced. When the amount of alcohol that is used exceeds 100 parts by weight, the yield and/or the percentage yield of the desired fatty acid ester that is obtained through the transesterification reaction no longer changes, but rather there is a risk that the production efficiency may be reduced.

Water that is used in the present invention may be any of distilled water, ion-exchanged water, tap water, and pure water.

The amount of the above-described water that is used in the present invention varies in accordance with, for example, the type and/or amount of raw fat or oil that is used, and is therefore not necessarily limited, but may be preferably 0.1 parts by weight to 50 parts by weight, and preferably 2 parts by weight to 30 parts by weight, relative to 100 parts by weight of raw fat or oil. When the amount of water that is used is less than 0.1 parts by weight, the amount of the water layer formed in the reaction system is insufficient, making it impossible for an effective transesterification reaction using the above-described raw fat or oil, liquid enzyme, and alcohol to occur, and there is thus a risk that the yield and/or the percentage yield of a desired fatty acid ester may be reduced. When the amount of water that is used exceeds 50 parts by weight, the yield and/or the percentage yield of the desired fatty acid ester that is obtained through the transesterification reaction no longer changes, but rather there is a risk that the production efficiency may be reduced.

The electrolyte that is used in the present invention is a substance that exhibits a predetermined conductivity when dissolved in the above-described water. Examples of anions constituting the electrolyte include, but not necessarily limited to, hydrogen carbonate ions, carbonate ions, chloride ions, hydroxide ions, citrate ions, hydrogen phosphate ions, dihydrogen phosphate ions, and phosphate ions, as well as combinations thereof. Examples of cations constituting the electrolyte include alkali metal ions and alkaline earth metal ions as well as combinations thereof, and more specifically include sodium ions, potassium ions, and calcium ions as well as combinations thereof. In the present invention, preferred examples of the electrolyte include sodium hydrogen carbonate (baking soda), sodium carbonate, calcium chloride, calcium hydroxide, trisodium citrate, sodium hydrogen phosphate, sodium dihydrogen phosphate, sodium chloride, and trisodium phosphate, as well as combinations thereof. Sodium hydrogen carbonate (baking soda) is more preferable because it is versatile and easily available, for example.

In the present invention, it is preferable that water and the above-described electrolyte are mixed in advance to prepare an aqueous electrolyte solution having a predetermined concentration, and the water and the electrolyte in the form of the aqueous electrolyte solution are added to the reaction system containing the above-described raw fat or oil, liquid enzyme, and alcohol.

Furthermore, it is preferable that the aqueous electrolyte solution that may be added has a predetermined conductivity. The aqueous electrolyte solution that may be prepared has a conductivity of preferably 30 mS/m to 5000 mS/m, more preferably 100 mS/m to 4500 mS/m, and even more preferably 200 mS/m to 4000 mS/m. When the aqueous electrolyte solution that is added has a conductivity of less than 30 mS/m, there are cases where it is difficult for the oil layer and the water layer in the reaction system to appropriately form an emulsion. When the aqueous electrolyte solution that is added has a conductivity of more than 5000 mS/m, there are cases where saponification of the raw fat or oil and/or a reduction in the reaction efficiency occurs.

Alternatively, in the present invention, it is preferable that the liquid enzyme, of the components to be added to the reaction system, is mixed with water and the electrolyte in advance to prepare an enzyme solution, and the liquid enzyme in the form of the enzyme solution is added to the reaction system containing the above-described raw fat or oil and alcohol. It should be noted that, in the present invention, the above-described enzyme solution can also be regarded as a type of the above-described aqueous electrolyte solution in that the liquid enzyme is added to water and the electrolyte.

Furthermore, it is preferable that the enzyme solution that may be added has a predetermined conductivity. The aqueous electrolyte solution that may be prepared has a conductivity of preferably 10 mS/m to 20000 mS/m, more preferably 100 mS/m to 10000 mS/m, and even more preferably 130 mS/m to 5000 mS/m. When the enzyme solution that is added has a conductivity of less than 10 mS/m, there are cases where it is difficult for the oil layer and the water layer in the reaction system to appropriately form an emulsion. When the enzyme solution that is added has a conductivity of more than 20000 mS/m, there are cases where saponification of the raw fat or oil and/or a reduction in the reaction efficiency occurs.

In the present invention, the above-described raw fat or oil, catalyst, and alcohol, as well as the above-described water and electrolyte (which encompass cases where the water and the electrolyte are added in the form of the above-described aqueous electrolyte solution or enzyme solution) are added into a single reaction vessel simultaneously or in any order and mixed together preferably under agitation, and thus, a fatty acid ester is generated through a transesterification reaction. The temperature that is applied during such a transesterification reaction is not necessarily limited, but may be, for example, 5° C. to 80° C., preferably 15° C. to 80° C., and more preferably 25° C. to 50° C.

It should be noted that, in the present invention, agitation of the reactants is not necessarily required to be performed at a high speed (e.g., 600 rpm or more). For example, the agitation may also be performed at a low speed (e.g., 80 rpm or more and less than 300 rpm) or a middle speed (e.g., 300 rpm or more and less than 600 rpm). Furthermore, the reaction time varies in accordance with the amount of each of the raw fat or oil, catalyst, and alcohol, as well as water and electrolyte (which encompass cases where the water and the electrolyte are added in the form of the above-described aqueous electrolyte solution or enzyme solution), and is therefore not necessarily limited. A person skilled in the art can set any desired period of time.

After the completion of the above-described transesterification reaction, the reaction solution is separated into a layer containing the fatty acid ester and a layer containing the by-product glycerin by using, for example, a method that is well-known to a person skilled in the art. After that, the layer containing the fatty acid ester may be further subjected to isolation and refining of the fatty acid ester by using a method that is well-known to a person skilled in the art, as necessary.

The fatty acid ester that is obtained in the above-described manner can be used as, for example, a biodiesel fuel or a constituent component thereof.

EXAMPLES

Hereinafter, the present invention will be described in detail using examples. However, the present invention is not limited to these examples.

Reference Example 1

Dependence of Transesterification Reaction on Agitation Speed

First, the effect of the agitation speed on a transesterification reaction in an oil-water two-phase system was investigated.

To five 50-mL screw cap bottles were added 9 g of waste cooking oil having an acid value of 0.9 mg-KOH/g, a liquid enzyme (liquid lipase; Callera Trans L, manufactured by Novozymes), 0.5 mL of distilled water (having a conductivity of 0.3 mS/m when measured in advance), and 3 M equivalents of methanol, followed by agitation at 35° C. and at an agitation speed of 100 rpm, 400 rpm, 600 rpm, 800 rpm, or 1000 rpm to perform transesterification reactions. During each of the reactions, the reaction solution in the reaction system was sampled as appropriate, and the methyl ester (ME) content in the reaction solution as well as the content of unreacted glycerides (monoglycerides (MG), diglycerides (DG), and triglycerides (TG)) were measured using gas chromatography (GC-2010 manufactured by Shimadzu Corporation). The obtained results are shown in FIG. 1.

As shown in FIG. 1(a), irrespective of the agitation speed at which agitation was performed, methyl esters generated in the reaction system increased with the passage of reaction time, and in particular, it can be seen that, at the same point in time, the higher the agitation speed, the greater the value of the methyl ester content. On the other hand, as shown in FIGS. 1(b) to 1(d), with regard to diglycerides and triglycerides of the unreacted glycerides, at the same point in time, the higher the agitation speed except at 100 rpm, the lower the values of the diglyceride content and the triglyceride content. From these results, it can be seen that, in the transesterification reactions performed in Reference Example 1, the agitation speed had a great effect on the content of methyl esters, which are the products, and the unreacted glyceride content, and, usually, a larger amount of target methyl esters can be generated by performing agitation at a high speed rather than by performing agitation at a low speed.

Example 1

Methyl Ester Production via Transesterification Reaction Under Low-Speed Agitation Conditions An aqueous solution (0.12 M) of sodium hydrogen carbonate was prepared by adding sodium hydrogen carbonate to distilled water (conductivity 0.3 mS/m, pH 6.5). The resulting aqueous solution of sodium hydrogen carbonate had a conductivity of 860 mS/m and a pH of 8.0. It should be noted that the conductivity was measured on a conductivity meter (LAQAtwin COND manufactured by HORIBA, Ltd.), and the pH was measured on a pH meter (LAQUAtwin pH manufactured by HORIBA, Ltd.).

To a 50-mL screw cap bottle were added 9 g of waste cooking oil having an acid value of 0.9 mg-KOH/g, 50 mg of a liquid enzyme (liquid lipase; Callera Trans L, manufactured by Novozymes), 0.5 mL of the aqueous solution of sodium hydrogen carbonate that was prepared as described above, and 3 M equivalents of methanol, followed by agitation at 35° C. and at an agitation speed of 100 rpm to perform a transesterification reaction. During the reaction, the reaction solution in the reaction system was sampled as appropriate, and the methyl ester (ME) content in the reaction solution was measured using gas chromatography (GC-2010 manufactured by Shimadzu Corporation). The obtained results are shown in FIG. 2.

Examples 2 and 3

Methyl Ester Production via Transesterification Reaction Under Low-Speed Agitation Conditions An aqueous solution (0.1 M) of sodium dihydrogen phosphate was prepared by adding sodium dihydrogen phosphate to distilled water (conductivity; 0.3 mS/m, pH 6.5) (Example 2). The resulting aqueous solution of sodium dihydrogen phosphate had a conductivity of 520 mS/m and a pH of 4.5.

On the other hand, an aqueous solution (0.1 M) of trisodium phosphate was prepared by adding trisodium phosphate to distilled water (conductivity; 0.3 mS/m, pH 6.5) (Example 3). The resulting aqueous solution of sodium dihydrogen phosphate had a conductivity of 4000 mS/m and a pH of 11.7.

Transesterification reactions were performed in the same manner as in Example 1 except that 0.5 mL of the above-described aqueous solution of sodium dihydrogen phosphate or 0.5 mL of the above-described aqueous solution of sodium dihydrogen phosphate was used instead of the aqueous solution of sodium hydrogen carbonate used in Example 1. During each of the reactions, the reaction solution in the reaction system was sampled as appropriate, and the methyl ester (ME) content in the reaction solution was measured using gas chromatography. The obtained results are shown in FIG. 2.

Comparative Examples 1 and 2

Methyl Ester Production in Transesterification Reaction Under Low-Speed Agitation Conditions Transesterification reactions were performed in the same manner as in Example 1 except that 0.5 mL of distilled water (conductivity; 0.3 mS/m, pH 6.5) (Comparative Example 1) or 0.5 mL of alkaline ionized water (conductivity; 15 mS/m, pH 9) (Comparative Example 2) was used instead of the aqueous solution of sodium hydrogen carbonate used in Example 1. During each of the reactions, the reaction solution in the reaction system was sampled as appropriate, and the methyl ester (ME) content in the reaction solution was measured using gas chromatography. The obtained results are shown in FIG. 2

As shown in FIG. 2, it can be seen that, in the systems in which the transesterification reactions were performed in the presence of the aqueous solution of sodium hydrogen carbonate (Example 1), the aqueous solution of sodium dihydrogen phosphate (Example 2), and trisodium phosphate (Example 3), respectively, which each served as the aqueous electrolyte solution, a large amount of methyl esters was generated from immediately after the start of the reaction, compared with the systems in which distilled water (Comparative Example 1) and alkaline ionized water (Comparative Example 2) were used instead of these aqueous solutions. It should be noted that, with respect to all of Examples 1 to 3, it can be seen that, in spite of the relatively slow agitation speed of 100 rpm, methyl esters were efficiently formed.

Example 4

Methyl Ester Production via Transesterification Reaction Under High-Speed Agitation Conditions To a 50-mL screw cap bottle were added 9 g of waste cooking oil having an acid value of 0.9 mg-KOH/g, 50 mg of a liquid enzyme (liquid lipase; Callera Trans L, manufactured by Novozymes), 0.5 mL of the aqueous solution of sodium hydrogen carbonate (conductivity 860 mS/m, pH 8.0) prepared in Example 1, and 3 M equivalents of methanol, followed by agitation at 35° C. and at an agitation speed of 800 rpm to perform a transesterification reaction. During the reaction, the reaction solution in the reaction system was sampled as appropriate, and the methyl ester (ME) content in the reaction solution as well as the content of unreacted glycerides (monoglycerides (MG), diglycerides (DG), and triglycerides (TG)) were measured using gas chromatography (GC-2010 manufactured by Shimadzu Corporation). The obtained results are shown in FIG. 3.

Comparative Example 3

Methyl Ester Production via Transesterification Reaction Under High-Speed Agitation Conditions A transesterification reaction was performed in the same manner as in Example 4 except that 0.5 mL of distilled water (conductivity; 0.3 mS/m, pH 6.5) was used instead of the aqueous solution of sodium hydrogen carbonate used in Example 4. During the reaction, the reaction solution in the reaction system was sampled as appropriate, and the methyl ester (ME) content in the reaction solution as well as the content of unreacted glycerides (monoglycerides (MG), diglycerides (DG), and triglycerides (TG)) were measured using gas chromatography. The obtained results are shown in FIG. 3.

As shown in FIG. 3, in the system (Example 4) in which the transesterification reaction was performed in the presence of the aqueous solution of sodium hydrogen carbonate serving as the aqueous electrolyte solution, a large amount of methyl esters was generated from immediately after the start of the reaction, compared with the system (Comparative Example 3) in which distilled water was used instead of the aqueous solution (FIG. 3(a)). On the other hand, with regard to the content of unreacted glycerides (FIGS. 3(b) to 3(d), at the same reaction time, the reaction system of Comparative Example 4 generally showed the higher values. From these results, it can be seen that, under the condition that agitation was performed at the relatively fast agitation speed of 800 rpm, in the reaction system of Example 4 in which the aqueous solution of sodium hydrogen carbonate was used, methyl esters were efficiently formed, compared with the reaction system of Comparative Example 3 in which distilled water was used.

Example 5

Transesterification Reactions Under Low-Speed Agitation with Repeated Use of Liquid Enzyme To a 50-mL screw cap bottle were added 9 g of waste cooking oil having an acid value of 0.9 mg-KOH/g, 50 mg of a liquid enzyme (liquid lipase; Callera Trans L, manufactured by Novozymes), 0.5 mL of the aqueous solution of sodium hydrogen carbonate (conductivity 860 mS/m, pH 8.0) prepared in Example 1, and 3 M equivalents of methanol, followed by agitation at 35° C. and at an agitation speed of 100 rpm to perform a transesterification reaction. During the reaction, the reaction solution in the reaction system was sampled as appropriate, and the methyl ester (ME) content in the reaction solution was measured using gas chromatography (GC-2010 manufactured by Shimadzu Corporation). The reaction was completed after 72 hours had elapsed from the start of the reaction. The above-described transesterification reaction was taken as the transesterification reaction of a first batch.

Next, the following procedures were performed as a transesterification reaction of a second batch.

After the completion of the reaction of the first batch, the resulting solution was allowed to stand overnight for separation, thereby separating methyl esters and a glycerin layer, and the methyl esters constituting the supernatant were removed. To the thus obtained glycerin layer (reaction residue) were newly added 9 g of waste cooking oil having an acid value of 0.9 mg-KOH/g, 0.5 mL of the aqueous solution of sodium hydrogen carbonate (conductivity 860 mS/m, pH 8.0) prepared in Example 1, and 3 M equivalents of methanol, followed by agitation at 35° C. and at an agitation speed of 100 rpm again to perform a transesterification reaction. Moreover, sampling was also performed during the reaction, and the methyl ester (ME) content in the reaction solution was measured. The above-described reaction was taken as the transesterification reaction of the second batch.

Furthermore, transesterification reactions of third to fifth batches using the respectively obtained glycerin layers (reaction residues) were performed in the same manner as described above, sampling was performed during each of the reactions, and the methyl ester (ME) content in each reaction solution was measured. The obtained results are shown in FIG. 4.

Comparative Example 4

Transesterification Reactions Under Low-Speed Agitation with Repeated Use of Liquid Enzyme A transesterification reaction of a first batch was performed in the same manner as in Example 5 except that 0.5 mL of distilled water (conductivity; 0.3 mS/m, pH 6.5) was used instead of the aqueous solution of sodium hydrogen carbonate used in Example 5. During the reaction, the reaction solution in the reaction system was sampled as appropriate, and the methyl ester (ME) content in the reaction solution was measured using gas chromatography.

After that, the generated methyl esters were removed in the same manner as in Example 5, and an attempt to perform a transesterification reaction of a second batch with respect to the obtained glycerin layer (reaction residue) was made. However, for the second and subsequent batches, the presence of methyl esters was not observed in the reaction systems. The obtained results are shown in FIG. 4.

As shown in FIG. 4, it can be seen that, in spite of the relatively low agitation speed of 100 rpm, in the reaction systems of Example 5 in which the respective transesterification reactions were performed in the presence of the aqueous solution of sodium hydrogen carbonate serving as the aqueous electrolyte solution, even though the liquid enzyme was repeatedly used from the second batch to at least the fifth batch, methyl esters were efficiently generated to a content of 75% or more. In contrast, in the reaction systems (Comparative Example 4) in which distilled water was used instead of the aqueous solution of sodium hydrogen carbonate, the generation of methyl esters at the above-described agitation speed was not sufficient even from the stage of the first batch, and repeated use of the liquid enzyme for the second and subsequent batches was also difficult.

Example 6

Transesterification Reactions Under Low-Speed Agitation with Repeated Use of Liquid Enzyme A transesterification reaction of a first batch was performed in the same manner as in Example 5.

Then, the following procedures were performed as a transesterification reaction of a second batch.

After the completion of the reaction of the first batch, the resulting solution was allowed to stand overnight for separation, thereby separating methyl esters and a glycerin layer, and the methyl esters constituting the supernatant were removed. To the thus obtained glycerin layer (reaction residue) were newly added 9 g of waste cooking oil having an acid value of 0.9 mg-KOH/g, 0.5 mL of distilled water (conductivity; 0.3 mS/m, pH 6.5), and 3 M equivalents of methanol, followed by agitation at 35° C. and at an agitation speed of 100 rpm again to perform a transesterification reaction. Moreover, sampling was also performed during the reaction, and the methyl ester (ME) content in the reaction solution was measured. The above-described reaction was taken as the transesterification reaction of the second batch.

Furthermore, transesterification reactions of third and fourth batches using the respectively obtained reaction residues were performed in the same manner as for the above-described second batch, sampling was performed during each of the reactions, and the methyl ester (ME) content in each reaction solution was measured.

The obtained results are shown in FIG. 5, which is superimposed on the results obtained in Example 5.

As shown in FIG. 5, from the first batch to the fourth batch, the methyl ester content obtained in Example 6 showed similar changes to those obtained in Example 5. Therefore, it can be seen that, for the second and subsequent batches, although the aqueous solution of sodium hydrogen carbonate (aqueous electrolyte solution) was not used in the reaction systems, methyl esters were efficiently generated while the liquid enzyme was repeatedly used, even under the condition that agitation was performed at the relatively low agitation speed (100 rpm).

Example 7

Transesterification Reactions Under High-Speed Agitation with Repeated Use of Liquid Enzyme To a 50-mL screw cap bottle were added 9 g of waste cooking oil having an acid value of 0.9 mg-KOH/g, 50 mg of a liquid enzyme (liquid lipase; Callera Trans L, manufactured by Novozymes), 0.5 mL of the aqueous solution of sodium hydrogen carbonate (conductivity 860 mS/m, pH 8.0) prepared in Example 1, and 3 M equivalents of methanol, followed by agitation at 35° C. and at an agitation speed of 800 rpm to perform a transesterification reaction. During the reaction, the reaction solution in the reaction system was sampled as appropriate, and the methyl ester (ME) content in the reaction solution was measured using gas chromatography (GC-2010 manufactured by Shimadzu Corporation). The reaction was completed after 72 hours had elapsed from the start of the reaction. The above-described reaction was taken as a transesterification reaction of a first batch.

Next, the following procedures were performed as a transesterification reaction of a second batch.

After the completion of the reaction of the first batch, the resulting solution was allowed to stand overnight for separation, thereby separating methyl esters and a glycerin layer, and the methyl esters constituting the supernatant were removed. To the thus obtained glycerin layer (reaction residue) were newly added 9 g of waste cooking oil having an acid value of 0.9 mg-KOH/g, 0.5 mL of the aqueous solution of sodium hydrogen carbonate (conductivity 860 mS/m, pH 8.0) prepared in Example 1, and 3 M equivalents of methanol, followed by agitation at 35° C. and at an agitation speed of 800 rpm again to perform a transesterification reaction. Moreover, sampling was also performed during the reaction, and the methyl ester (ME) content in the reaction solution was measured. The above-described reaction was taken as the transesterification reaction of the second batch.

Furthermore, transesterification reactions of third to twelfth batches using the respectively obtained glycerin layers (reaction residues) were performed in the same manner as described above, sampling was performed during each of the reactions, and the methyl ester (ME) content in each reaction solution was measured. The obtained results are shown in FIG. 6.

Comparative Example 5

Transesterification Reactions Under High-Speed Agitation with Repeated Use of Liquid Enzyme A transesterification reaction of a first batch was performed in the same manner as in Example 7 except that 0.5 mL of distilled water (conductivity; 0.3 mS/m, pH 6.5) was used instead of the aqueous solution of sodium hydrogen carbonate used in Example 7. During the reaction, the reaction solution in the reaction system was sampled as appropriate, and the methyl ester (ME) content in the reaction solution was measured using gas chromatography.

After that, the generated methyl esters were removed in the same manner as in Example 7, and an attempt to perform transesterification reactions of second to fourth batches with respect to the respectively obtained glycerin layers (reaction residues) was made. However, for the fifth and subsequent batches, the presence of methyl esters was not observed in the reaction systems. The obtained results are shown in FIG. 6.

As shown in FIG. 6, in Comparative Example 5, even though a methyl ester content of about 90% by weight was finally achieved for the first batch, the value of the highest content for each batch gradually decreased from the second batch (finally about 80% by weight) to the third batch (finally about 35% by weight), and almost no methyl ester was generated for the fourth batch. In contrast, in Example 7, transesterification could be repeated as many as at least twelve times. In particular, for each of the first to sixth batches, a methyl ester content of 80% by weight or more was finally achieved, and for all of the first to twelfth batches, a methyl ester content of about 70% by weight or more was finally achieved. From these results, it can be seen that, under the condition that agitation was performed at the relatively fast agitation speed (800 rpm), the repeated use of the liquid enzyme could be further extended, and methyl esters were thus even more efficiently generated.

Example 8

Transesterification Reaction Using Modified Fat or Oil

A circulating transesterification device was produced based on the method described in a previously reported document (Seibutsu-kogaku Kaishi, 2014, Vol. 92, No. 6, pp. 262-269), and a fatty acid ester and a by-product glycerin were produced from waste cooking oil in the following manner.

First, produced as the circulating transesterification device were a raw material tank (having a capacity of 250 L), a catalytic reaction tube (which is constituted by a stainless steel pipe having a length of 1.7 m, an internal diameter of 210.0 mm, and an internal volume of 58851.5 mL, and the inside of which is packed with an enzyme catalyst (lipase derived from Candida antarctica B (Novozyme 435: manufactured by Novozymes)) immobilized on a carrier (ion exchange resin)) for subjecting a material supplied from the raw material tank to a transesterification reaction, a separating vessel (having a capacity of 40 L) for separating a reaction solution obtained from the catalytic reaction tube in accordance with ingredients thereof and allowing one of the separated ingredients to overflow therefrom, and a device for collecting the by-product glycerin precipitated in the separating vessel as a result of the overflowing from the separating vessel as crude glycerin.

Next, to the raw material tank of the circulating transesterification device were added 200 L of waste cooking oil and methanol (an amount of methanol corresponding to 0.5 mol equivalents with respect to the fat or oil (waste cooking oil) was manually added at the start of the reaction), followed by appropriate mixing and agitation. Then, the resulting mixture was supplied to the catalytic reaction tube and subjected to a transesterification reaction at 30° C. The reaction solution that had undergone transesterification was transferred from the catalytic reaction tube to the separating vessel, a layer containing the generated fatty acid ester was allowed to overflow from the separating vessel, and the by-product glycerin precipitated in the separating vessel was collected as crude glycerin. Moreover, until 13.5 hours had elapsed after the start of the reaction, methanol was supplied to the raw material tank at a rate of 2.1 kg/hour by using a metering pump. In this manner, the reaction solution was circulated in the device.

After the operation of circulating the reaction solution from the catalytic reaction tube to the raw material tank was continued for about 24 hours, a portion of glycerin (crude glycerin) was collected from the separating vessel. It was confirmed that this crude glycerin contained, relative to the total weight thereof, about 80% pure glycerin, about 10% methanol, and other oil contents such as a fatty acid ester. The pH of the crude glycerin was acidic to some extent, and when examined by using a pH checker for biodiesel fuel (manufactured by Filtertechnik), the pH was 4.5. Based on these results, it was confirmed that the obtained crude glycerin was glycerin (glycerin derived from an enzyme-catalyzed process) that contained substantially no alkaline impurities.

Furthermore, to a 30-mL screw cap bottle were added 9 g of waste cooking oil having an acid value of 0.9 mg-KOH/g fat or oil and 0.84 g of the crude glycerin that was obtained as described above, and furthermore, a stirrer bar was placed in the bottle to perform agitation at 25° C. for 10 minutes, followed by centrifugation at 13,000 rpm for 3 minutes to give a modified fat or oil. The acid value of the thus obtained modified fat or oil was measured through neutralization titration (JIS K 250) using potassium hydroxide and found to be 0.4 mg-KOH/g fat or oil.

Next, to a 50-mL screw cap bottle were added 9 g of the modified oil that was prepared as described above and that had an acid value of 0.4 mg-KOH/g, 50 mg of a liquid enzyme (liquid lipase; Callera Trans L, manufactured by Novozymes), 0.5 mL of the aqueous solution of sodium hydrogen carbonate (conductivity 860 mS/m, pH 8.0) prepared in Example 1, and 3 M equivalents of methanol, followed by agitation at 35° C. and at an agitation speed of 100 rpm to perform a transesterification reaction. During the reaction, the reaction solution in the reaction system was sampled as appropriate, and the methyl ester (ME) content in the reaction solution as well as the content of unreacted glycerides (monoglycerides (MG), diglycerides (DG), and triglycerides (TG)) were measured using gas chromatography (GC-2010 manufactured by Shimadzu Corporation). The obtained results are shown in FIG. 7.

Example 9

A transesterification reaction was performed in the same manner as in Example 8 except that 9 g of waste cooking oil having an acid value of 0.9 mg-KOH/g fat or oil was used instead of the modified fat or oil used in Example 8. During the reaction, the reaction solution in the reaction system was sampled as appropriate, and the methyl ester (ME) content in the reaction solution as well as the content of unreacted glycerides (monoglycerides (MG), diglycerides (DG), and triglycerides (TG)) were measured using gas chromatography. The obtained results are shown in FIG. 7.

Comparative Example 6

A transesterification reaction was performed in the same manner as in Example 8 except that 9 g of waste cooking oil having an acid value of 0.9 mg-KOH/g fat or oil was used instead of the modified fat or oil used in Example 8, and 0.5 mL of distilled water (conductivity; 0.3 mS/m, pH 6.5) was used instead of the aqueous solution of sodium hydrogen carbonate used in Example 8. During the reaction, the reaction solution in the reaction system was sampled as appropriate, and the methyl ester (ME) content in the reaction solution as well as the content of unreacted glycerides (monoglycerides (MG), diglycerides (DG), and triglycerides (TG)) were measured using gas chromatography. The obtained results are shown in FIG. 7.

As shown in FIG. 7(a), in the reaction systems (Examples 8 and 9) in which the aqueous solution of sodium hydrogen carbonate was used in the respective transesterification reactions, in spite of the relatively low agitation speed (100 rpm), the methyl ester content was increased compared with that in the reaction system (Comparative Example 6) in which the above-described aqueous solution was not used. Meanwhile, as shown in FIG. 7(d), it can be seen that, in the reaction system of Comparative Example 6, the unreacted triglyceride content was higher than those of Examples 8 and 9. Moreover, in the reaction system (Example 8) in which the above-described modified fat or oil was used, an even higher methyl ester content was achieved (FIG. 7(a)) compared with that in the reaction system (Example 9) in which the unmodified fat or oil was used. On the other hand, it can be seen that the unreacted glyceride content of Example 8 consistently showed a lower value than that of Example 9 (FIGS. 7(b) to 7(d)). From these results, it can be seen that the use of the modified fat or oil, which was obtained by using the by-product glycerin, for the transesterification reaction together with the aqueous solution of sodium hydrogen carbonate made it possible to further enhance the generation efficiency of methyl esters to be obtained.

Example 10

Effect on Inhibitor

Waste cooking oil containing a surfactant that inhibits a transesterification reaction was used, and whether or not the reaction was inhibited was examined.

A surfactant-containing fat or oil was prepared by dissolving, in waste cooking oil having an acid value of 0.9 mg-KOH/g, an anionic surfactant AOT (Aerosol OT; manufactured by Wako Pure Chemical Industries, Ltd.) capable of forming inverted micelles to a concentration of 1% by weight.

To a 50-mL screw cap bottle were added 9 g of the surfactant-containing fat or oil prepared as described above, 50 mg of a liquid enzyme (liquid lipase; Callera Trans L, manufactured by Novozymes), 0.5 mL of the aqueous solution of sodium hydrogen carbonate prepared in Example 1, and 3 M equivalents of methanol, followed by agitation at 35° C. and at an agitation speed of 800 rpm to perform a transesterification reaction. During the reaction, the reaction solution in the reaction system was sampled as appropriate, and the methyl ester (ME) content in the reaction solution was measured using gas chromatography (GC-2010 manufactured by Shimadzu Corporation). The obtained results are shown in FIG. 8.

Comparative Example 7

Effect on Inhibitor

A transesterification reaction with respect to the surfactant-containing fat or oil was performed in the same manner as in Example 4 except that 0.5 mL of distilled water (conductivity; 0.3 mS/m, pH 6.5) was used instead of the aqueous solution of sodium hydrogen carbonate used in Example 10. During the reaction, the reaction solution in the reaction system was sampled as appropriate, and the methyl ester (ME) content in the reaction solution was measured using gas chromatography. The obtained results are shown in FIG. 8.

As shown in FIG. 8, in the case where distilled water was used (Comparative Example 7), almost no generation of methyl esters was observed in the reaction system containing the surfactant-containing fat or oil (FIG. 8). Therefore, it can be seen that the anionic surfactant added to the waste cooking oil functioned as an inhibitory substance of the transesterification reaction and suppressed or interrupted the generation of methyl esters. In contrast, in the case where the aqueous solution of sodium hydrogen carbonate was used (Example 10), generation of methyl esters was observed even though the reaction system contained the surfactant-containing fat or oil, and it can be seen that the methyl ester content increased with the passage of the reaction time (FIG. 8). From these results, it can be seen that even if the raw fat or oil contains an inhibitory substance such as an anionic surfactant, the use of an aqueous electrolyte solution such as the aqueous solution of sodium hydrogen carbonate makes it possible to produce a desired fatty acid ester while reducing the effect of the inhibitory substance.

Example 11

Effect of Various Raw Fats and Oils (1)

To a 50-mL screw cap bottle were added 9 g of rapeseed oil (conductivity; 4.3 mS/m; unrefined fat or oil), 50 mg of a liquid enzyme (liquid lipase; Callera Trans L, manufactured by Novozymes), 0.5 mL of the aqueous solution of sodium hydrogen carbonate prepared in Example 1, and 3 M equivalents of methanol, followed by agitation at 35° C. and at an agitation speed of 800 rpm to perform a transesterification reaction for 72 hours. After the completion of the reaction, the methyl ester (ME) content in the reaction solution as well as the content of unreacted glycerides (monoglycerides (MG), diglycerides (DG), and triglycerides (TG)) were measured using gas chromatography. The obtained results are shown in Table 1.

Comparative Example 8

Effect of Various Raw Fats and Oils (1)

A transesterification reaction was performed in the same manner as in Example 11 except that 0.5 mL of distilled water (conductivity; 0.3 mS/m, pH 6.5) was used instead of the aqueous solution of sodium hydrogen carbonate used in Example 11. After the completion of the reaction, the methyl ester (ME) content in the reaction solution and the unreacted glyceride content were measured using gas chromatography. The obtained results are shown in Table 1.

TABLE 1

|  | Example 11 | Comparative Example 8 |
| --- | --- | --- |
| Raw fat and oil | Rapeseed oil (Unrefined) | |
| Added water phase ingredient | NaHCO$_3$ aq | Distilled water |
| Methylester (ME) content[1] | 82.009 | 66.880 |
| Monoglycerides (MG) content[1] | 0.617 | 5.237 |
| Diglycerides (DG) content[1] | 5.975 | 15.181 |
| Triglycerides (TG) content[1] | 3.502 | 5.017 |

[1]Content in the reaction solution after the completion of the reaction (% by weight)

Example 12

Effect of Various Raw Fats and Oils (2)

To a 50-mL screw cap bottle were added 9 g of waste cooking oil (conductivity; 8.7 mS/m) having a thermal degradation of fats and oils of acid value 4, 50 mg of a liquid enzyme (liquid lipase; Callera Trans L, manufactured by Novozymes), 0.5 mL of the aqueous solution of sodium hydrogen carbonate prepared in Example 1, and 3 M equivalents of methanol, followed by agitation at 35° C. and at an agitation speed of 800 rpm to perform a transesterification reaction for 72 hours. After the completion of the reaction, the methyl ester (ME) content in the reaction solution as well as the content of unreacted glycerides (monoglycerides (MG), diglycerides (DG), and triglycerides (TG)) were measured using gas chromatography. The obtained results are shown in Table 2.

Comparative Example 9

Effect of Various Raw Fats and Oils (2)

A transesterification reaction was performed in the same manner as in Example 12 except that 0.5 mL of distilled water (conductivity; 0.3 mS/m, pH 6.5) was used instead of the aqueous solution of sodium hydrogen carbonate used in Example 12. After the completion of the reaction, the methyl ester (ME) content in the reaction solution and the unreacted glyceride content were measured using gas chromatography. The obtained results are shown in Table 2.

TABLE 2

|  | Example 12 | Comprative Example 9 |
| --- | --- | --- |
| Raw fat and oil | Waste cooking oil (AV4) | |
| Added water phase ingredient | NaHCO$_3$ aq | Distilled water |
| Methylester (ME) content[1] | 73.274 | 54.598 |
| Monoglycerides (MG) content[1] | 1.181 | 3.729 |
| Diglycerides (DG) content[1] | 4.989 | 15.308 |
| Triglycerides (TG) content[1] | 2.461 | 5.682 |

[1]Content in the reaction solution after the completion of the reaction (% by weight)

Example 13

Effect of Various Raw Fats and Oils (3)

To a 50-mL screw cap bottle were added 9 g of waste cooking oil (conductivity; 11.3 mS/m) having a thermal degradation of fats and oils of acid value 6, 50 mg of a liquid enzyme (liquid lipase; Callera Trans L, manufactured by Novozymes), 0.5 mL of the aqueous solution of sodium hydrogen carbonate prepared in Example 1, and 3 M equivalents of methanol, followed by agitation at 35° C. and at an agitation speed of 800 rpm to perform a transesterification reaction for 72 hours. After the completion of the reaction, the methyl ester (ME) content in the reaction solution as well as the content of unreacted glycerides (monoglycerides (MG), diglycerides (DG), and triglycerides (TG)) were measured using gas chromatography. The obtained results are shown in Table 3.

Comparative Example 10

Effect of Various Raw Fats and Oils (3)

A transesterification reaction was performed in the same manner as in Example 13 except that 0.5 mL of distilled water (conductivity; 0.3 mS/m, pH 6.5) was used instead of the aqueous solution of sodium hydrogen carbonate used in Example 13. After the completion of the reaction, the methyl ester (ME) content in the reaction solution and the unreacted glyceride content were measured using gas chromatography. The obtained results are shown in Table 3.

TABLE 3

|  | Example 13 | Comparative Example 10 |
| --- | --- | --- |
| Raw fat and oil | Waste cooking oil (AV6) | |
| Added water phase ingredient | NaHCO$_3$ aq | Distilled water |
| Methylester (ME) content[1] | 68.375 | 66.043 |
| Monoglycerides (MG) content[1] | 0.716 | 1.532 |
| Diglycerides (DG) content[1] | 2.706 | 7.799 |
| Triglycerides (TG) content[1] | 1.504 | 3.295 |

[1]Content in the reaction solution after the completion of the reaction (% by weight)

Example 14

Effect of Various Raw Fats and Oils (4)

To a 50-mL screw cap bottle were added 9 g of waste cooking oil (conductivity; 9.0 mS/m) having a thermal degradation of fats and oils of acid value 8, 50 mg of a liquid enzyme (liquid lipase; Callera Trans L, manufactured by Novozymes), 0.5 mL of the aqueous solution of sodium hydrogen carbonate prepared in Example 1, and 3 M equivalents of methanol, followed by agitation at 35° C. and at an agitation speed of 800 rpm to perform a transesterification reaction for 72 hours. After the completion of the reaction, the methyl ester (ME) content in the reaction solution as well as the content of unreacted glycerides (monoglycerides (MG), diglycerides (DG), and triglycerides (TG)) were measured using gas chromatography. The obtained results are shown in Table 4.

Comparative Example 11

Effect of Various Raw Fats and Oils (4)

A transesterification reaction was performed in the same manner as in Example 14 except that 0.5 mL of distilled water (conductivity; 0.3 mS/m, pH 6.5) was used instead of the aqueous solution of sodium hydrogen carbonate used in Example 14. After the completion of the reaction, the methyl ester (ME) content in the reaction solution and the unreacted glyceride content were measured using gas chromatography. The obtained results are shown in Table 4.

TABLE 4

|  | Example 14 | Comparative Example 11 |
| --- | --- | --- |
| Raw fat and oil | Waste cooking oil (AV8) | |
| Added water phase ingredient | NaHCO$_3$ aq | Distilled water |
| Methylester (ME) content[1] | 64.778 | 56.365 |
| Monoglycerides (MG) content[1] | 1.171 | 1.561 |
| Diglycerides (DG) content[1] | 4.107 | 6.838 |
| Triglycerides (TG) content[1] | 1.498 | 3.462 |

[1]Content in the reaction solution after the completion of the reaction (% by weight)

Example 15

Effect of Various Raw Fats and Oils (5)

To a 50-mL screw cap bottle were added 4.5 g of unheated solid beef tallow, 50 mg of a liquid enzyme (liquid lipase; Callera Trans L, manufactured by Novozymes), 0.5 mL of the aqueous solution of sodium hydrogen carbonate prepared in Example 1, and 3 M equivalents of methanol, followed by agitation at 35° C. and at an agitation speed of 800 rpm to perform a transesterification reaction for 72 hours. After the completion of the reaction, the methyl ester (ME) content in the reaction solution as well as the content of unreacted glycerides (monoglycerides (MG), diglycerides (DG), and triglycerides (TG)) were measured using gas chromatography. The obtained results are shown in Table 5.

Comparative Example 12

Effect of Various Raw Fats and Oils (5)

A transesterification reaction was performed in the same manner as in Example 15 except that 0.5 mL of distilled water (conductivity; 0.3 mS/m, pH 6.5) was used instead of the aqueous solution of sodium hydrogen carbonate used in Example 15. After the completion of the reaction, the methyl ester (ME) content in the reaction solution and the unreacted glyceride content were measured using gas chromatography. The obtained results are shown in Table 5.

TABLE 5

|  | Example 15 | Comparative Example 12 |
|---|---|---|
| Raw fat and oil | Beef tallow (unheated) | |
| Added water phase ingredient | NaHCO$_3$ aq | Distilled water |
| Methylester (ME) content[1] | 78.496 | 72.820 |
| Monoglycerides (MG) content[1] | 0.434 | 2.432 |
| Diglycerides (DG) content[1] | 2.379 | 10.168 |
| Triglycerides (TG) content[1] | 2.138 | 5.370 |

[1] Content in the reaction solution after the completion of the reaction (% by weight)

Example 16

Effect of Various Raw Fats and Oils (6)

To a 50-mL screw cap bottle were added 9 g of waste cooking oil (conductivity; 4.7 mS/m) to which phospholipid was added in a ratio of 5% by weight, 50 mg of a liquid enzyme (liquid lipase; Callera Trans L, manufactured by Novozymes), 0.5 mL of the aqueous solution of sodium hydrogen carbonate prepared in Example 1, and 3 M equivalents of methanol, followed by agitation at 35° C. and at an agitation speed of 800 rpm to perform a transesterification reaction for 72 hours. After the completion of the reaction, the methyl ester (ME) content in the reaction solution as well as the content of unreacted glycerides (monoglycerides (MG), diglycerides (DG), and triglycerides (TG)) were measured using gas chromatography. The obtained results are shown in Table 6.

Comparative Example 13

Effect of Various Raw Fats and Oils (6)

A transesterification reaction was performed in the same manner as in Example 16 except that 0.5 mL of distilled water (conductivity; 0.3 mS/m, pH 6.5) was used instead of the aqueous solution of sodium hydrogen carbonate used in Example 16. After the completion of the reaction, the methyl ester (ME) content in the reaction solution and the unreacted glyceride content were measured using gas chromatography. The obtained results are shown in Table 6.

TABLE 6

|  | Example 16 | Comparative Example 13 |
|---|---|---|
| Raw fat and oil | Waste cooking oil containing 5 wt % of phospholipid | |
| Added water phase ingredient | NaHCO$_3$ aq | Distilled water |
| Methylester (ME) content[1] | 86.452 | 83.480 |
| Monoglycerides (MG) content[1] | 0.228 | 0.235 |
| Diglycerides (DG) content[1] | 0.318 | 0.487 |
| Triglycerides (TG) content[1] | 0.068 | 0.150 |

[1] Content in the reaction solution after the completion of the reaction (% by weight)

Example 17

Effect of Various Raw Fats and Oils (7)

To a 50-mL screw cap bottle were added 9 g of waste cooking oil (conductivity; 4.0 mS/m) to which phospholipid was added in a ratio of 10% by weight, 50 mg of a liquid enzyme (liquid lipase; Callera Trans L, manufactured by Novozymes), 0.5 mL of the aqueous solution of sodium hydrogen carbonate prepared in Example 1, and 3 M equivalents of methanol, followed by agitation at 35° C. and at an agitation speed of 800 rpm to perform a transesterification reaction for 72 hours. After the completion of the reaction, the methyl ester (ME) content in the reaction solution as well as the content of unreacted glycerides (monoglycerides (MG), diglycerides (DG), and triglycerides (TG)) were measured using gas chromatography. The obtained results are shown in Table 7.

Comparative Example 14

Effect of Various Raw Fats and Oils (7)

A transesterification reaction was performed in the same manner as in Example 17 except that 0.5 mL of distilled water (conductivity; 0.3 mS/m, pH 6.5) was used instead of the aqueous solution of sodium hydrogen carbonate used in Example 17. After the completion of the reaction, the methyl ester (ME) content in the reaction solution and the unreacted glyceride content were measured using gas chromatography. The obtained results are shown in Table 7.

TABLE 7

|  | Example 17 | Comparative Example 14 |
|---|---|---|
| Raw fat and oil | Waste cooking oil containing 10 wt % of phospholipid | |
| Added water phase ingredient | NaHCO$_3$ aq | Distilled water |
| Methylester (ME) content[1] | 91.399 | 87.770 |
| Monoglycerides (MG) content[1] | 0.187 | 0.214 |
| Diglycerides (DG) content[1] | 0.262 | 0.271 |
| Triglycerides (TG) content[1] | 0.026 | 0.082 |

[1] Content in the reaction solution after the completion of the reaction (% by weight)

Example 18

Effect of Various Raw Fats and Oils (8)

To a 50-mL screw cap bottle were added 9 g of unrefined palm oil (conductivity; 2.2 mS/m), 50 mg of a liquid enzyme (liquid lipase; Callera Trans L, manufactured by Novozymes), 0.5 mL of the aqueous solution of sodium hydrogen carbonate prepared in Example 1, and 3 M equivalents of methanol, followed by agitation at 35° C. and at an agitation speed of 800 rpm to perform a transesterification reaction for 72 hours. After the completion of the reaction, the methyl ester (ME) content in the reaction solution as well as the content of unreacted glycerides (monoglycerides (MG), diglycerides (DG), and triglycerides (TG)) were measured using gas chromatography. The obtained results are shown in Table 8.

Comparative Example 15

Effect of Various Raw Fats and Oils (8)

A transesterification reaction was performed in the same manner as in Example 18 except that 0.5 mL of distilled water (conductivity; 0.3 mS/m, pH 6.5) was used instead of the aqueous solution of sodium hydrogen carbonate used in Example 18. After the completion of the reaction, the methyl ester (ME) content in the reaction solution and the unreacted glyceride content were measured using gas chromatography. The obtained results are shown in Table 8.

TABLE 8

|  | Example 18 | Comparative Example15 |
|---|---|---|
| Raw fat and oil | Unrefined palm oil | |
| Added water phase ingredient | NaHCO$_3$ aq | Distilled water |
| Methylester (ME) content[1] | 93.12 | 90.46 |
| Monoglycerides (MG) content[1] | 0.318 | 0.424 |
| Diglycerides (DG) content[1] | 1.398 | 2.711 |
| Triglycerides (TG) content[1] | 0.845 | 1.930 |

[1]Content in the reaction solution after the completion of the reaction (% by weight)

As shown in Tables 1 to 8, in the transesterification reactions using the various raw fats and oils, in all of the systems (Examples 11 to 18) in which the aqueous solution of sodium hydrogen carbonate was present as the aqueous electrolyte solution, a large amount of methyl esters was generated, while the unreacted glyceride content showed a low value, compared with the systems (Comparative Examples 8 to 15) in which distilled water was used instead of the aqueous solution. From these results, it can be seen that, with respect to the various raw fats and oils, in the reaction systems of Examples 11 to 18 in which the aqueous solution of sodium hydrogen carbonate was used, methyl esters were more efficiently generated while unreacted glycerides were reduced, compared with the reaction systems of Comparative Examples 8 to 15 in which distilled water was used.

Example 19

Dependence of Transesterification Reaction on Electrolyte Concentration

To four 50-mL screw cap bottles were added 9 g of waste cooking oil having an acid value of 0.9 mg-KOH/g, 50 mg of a liquid enzyme (liquid lipase; Callera Trans L, manufactured by Novozymes), 0.5 mL of distilled water (having a conductivity of 0.3 mS/m when measured in advance), 3 M equivalents of methanol, and 0.9 mg, 4.5 mg, 9 mg, or 90 mg (respectively corresponding to addition concentrations of 0.01% by weight, 0.05% by weight, 0.10% by weight, and 1.00% by weight) of sodium hydrogen carbonate serving as the electrolyte, followed by agitation at 35° C. and at an agitation speed of 100 rpm to perform transesterification reactions. During each of the reactions, the reaction solution in the reaction system was sampled as appropriate, and the methyl ester (ME) content in the reaction solution was measured using gas chromatography (GC-2010 manufactured by Shimadzu Corporation). The obtained results are shown in FIG. 9.

Comparative Example 16

Dependence of Transesterification Reaction on Electrolyte Concentration

A transesterification reaction was performed in the same manner as in Example 19 except that sodium hydrogen carbonate was not added. During the reaction, the reaction solution in the reaction system was sampled as appropriate, and the methyl ester (ME) content in the reaction solution was measured using gas chromatography. The obtained results are shown in FIG. 9.

As shown in FIG. 9, in all of the cases where the electrolyte (sodium hydrogen carbonate) was directly added to the reaction systems without preparing an aqueous electrolyte solution in advance, a large amount of methyl esters was generated, compared with the reaction system (Comparative Example 16) in which the electrolyte was not added. From these results, it can be seen that an electrolyte can be added to a reaction system regardless of whether the electrolyte is in solid form or in the form of an aqueous solution, and methyl esters were efficiently formed.

Example 20

Dependence of Transesterification Reaction on Conductivity of Enzyme Solution An enzyme solution was prepared by adding 0.5 g of a 10% by weight aqueous solution of sodium hydrogen carbonate to 50 mg of a liquid enzyme (liquid lipase; Callera Trans L, manufactured by Novozymes). The resulting enzyme solution had a conductivity of 1800 mS/m.

Next, to two 50-mL screw cap bottles were added 9 g of waste cooking oil having an acid value of 0.9 mg-KOH/g, 3 M equivalents of methanol, and the enzyme solution (whole amount) prepared as described above, followed by agitation at 35° C. and at an agitation speed of 800 rpm to perform transesterification reactions. During each of the reactions, the reaction solution in the reaction system was sampled as appropriate, and the methyl ester (ME) content in the reaction solution was measured using gas chromatography (GC-2010 manufactured by Shimadzu Corporation). The obtained results are shown in FIG. 10.

Comparative Example 17

Dependence of Transesterification Reaction on Conductivity of Enzyme Solution An enzyme solution was prepared in the same manner as in Example 20 except that 0.5 g of water was used instead of the aqueous solution of sodium hydrogen carbonate. The resulting enzyme solution had a conductivity of 129 mS/m.

Transesterification reactions using waste cooking oil and methanol were performed in the same manner as in Example 20 except that the above-described enzyme solution was used. During each of the reactions, the reaction solution in the reaction system was sampled as appropriate, and the methyl ester (ME) content in the reaction solution was measured using gas chromatography. The obtained results are shown in FIG. 10.

As shown in FIG. 10, even in the case (Example 20) where the enzyme solution prepared in advance and having a high conductivity was added to the reaction systems instead of the aqueous electrolyte solution, the amount of remaining triglycerides decreased compared with that of the reaction systems (Comparative Example 17) to which the enzyme solution having a low conductivity was added. Moreover, with the decrease in the amount of remaining triglycerides, the amount of generated methyl esters increased. From these results, it can be seen that when the electrolyte was added to the reaction system, the efficiency of formation of methyl esters was enhanced also by increasing the conductivity of the enzyme solution.

INDUSTRIAL APPLICABILITY

According to the present invention, a fatty acid ester can be efficiently produced. The fatty acid ester that is obtained according to the present invention is useful as, for example, a biodiesel fuel or a constituent component thereof.

The invention claimed is:

1. A method for producing a fatty acid ester comprising:
   mixing a raw fat or oil, a liquid lipase, and an alcohol having 1 to 8 carbon atoms in the presence of water and an electrolyte for transesterification reaction;
   removing the resultant fatty acid ester to remain the liquid enzyme in a residue; and
   using the residue as the liquid enzyme in the next mixing for the transesterification reaction;
   wherein the electrolyte comprises at least one salt selected from the group consisting of sodium hydrogen carbonate.

2. The method of claim 1, wherein the water and the electrolyte are added in the form of an aqueous electrolyte solution that has been prepared in advance.

3. The method of claim 2, wherein the aqueous electrolyte solution has a conductivity of 30 mS/m to 5000 mS/m.

4. The method of claim 1, wherein the liquid lipase is added together with the water and the electrolyte in the form of an enzyme solution that has been prepared in advance.

5. The method of claim 4, wherein the enzyme solution has a conductivity of 10 mS/m to 20000 mS/m.

6. The method of claim 1, wherein the raw fat or oil is at least one fat or oil selected from the group consisting of vegetable fats and oils, animal fats and oils, fish oils, fats and oils produced by microorganisms, and waste oils thereof.

7. The method of claim 1, wherein the raw fat or oil is a modified fat or oil that is obtained by mixing at least one fat or oil selected from the group consisting of vegetable fats and oils, animal fats and oils, fish oils, fats and oils produced by microorganisms, and waste oils thereof with glycerin derived from an enzyme-catalyzed process.

* * * * *